United States Patent
Rabolt et al.

(10) Patent No.: US 9,897,547 B2
(45) Date of Patent: Feb. 20, 2018

(54) GOLD NANOROD/POLYMER NANOCOMPOSITES AND SENSORS BASED THEREON

(71) Applicants: John F. Rabolt, Newark, DE (US); Wenqiong Tang, Newark, DE (US); D. Bruce Chase, Newark, DE (US); Donald L. Sparks, Newark, DE (US)

(72) Inventors: John F. Rabolt, Newark, DE (US); Wenqiong Tang, Newark, DE (US); D. Bruce Chase, Newark, DE (US); Donald L. Sparks, Newark, DE (US)

(73) Assignee: UNIVERSITY OF DELAWARE, Newark, DE (US)

( * ) Notice: Subject to any disclaimer, the term of this patent is extended or adjusted under 35 U.S.C. 154(b) by 0 days.

(21) Appl. No.: 14/775,269

(22) PCT Filed: Mar. 12, 2014

(86) PCT No.: PCT/US2014/023994
§ 371 (c)(1),
(2) Date: Sep. 11, 2015

(87) PCT Pub. No.: WO2014/159521
PCT Pub. Date: Oct. 2, 2014

(65) Prior Publication Data
US 2016/0069811 A1    Mar. 10, 2016

Related U.S. Application Data

(60) Provisional application No. 61/781,064, filed on Mar. 14, 2013.

(51) Int. Cl.
*G01N 21/65*      (2006.01)
*B82Y 30/00*      (2011.01)
(Continued)

(52) U.S. Cl.
CPC ............ *G01N 21/658* (2013.01); *B01J 31/06* (2013.01); *B32B 5/028* (2013.01); *B32B 5/26* (2013.01);
(Continued)

(58) Field of Classification Search
None
See application file for complete search history.

(56) References Cited

U.S. PATENT DOCUMENTS 8,349,131 B1 *   1/2013   Agarwal ................. D21F 11/00
                                                            162/138
8,921,473 B1 *  12/2014   Hyman .................... C08K 3/04
                                                            423/445 R
(Continued)

OTHER PUBLICATIONS

Carron, K., et al., "Selective-ultratrace detection of metal ions with SERS," 1991, pp. 420-423, vol. 45, No. 3, Applied Spectroscopy.
(Continued)

*Primary Examiner* — Melanie Yu Brown
(74) *Attorney, Agent, or Firm* — RatnerPrestia (57) ABSTRACT

A nanocomposite structure includes:
a) a charged fibrous substrate including fibers having disposed on their surfaces a multilayer structure including a layer of a first polyelectrolyte and disposed thereon a layer of a second polyelectrolyte of opposite charge from the first, the second polyelectrolyte forming the outermost layer of the charged fibrous substrate; and
b) charged nanorods having a charge opposite that of the charged fibrous substrate, including gold nanorods each having disposed on its surface one or more layers, the outermost of which is a third polyelectrolyte having a charge opposite that of the second polyelectrolyte, wherein the first and third polyelectrolytes may be the same or different;

(Continued)

wherein the charged nanorods are disposed unaligned with respect to each other on the charged fibrous substrate.

15 Claims, 8 Drawing Sheets

(51) Int. Cl.
| | |
|---|---|
| B32B 5/02 | (2006.01) |
| B32B 5/26 | (2006.01) |
| B01J 31/06 | (2006.01) |
| D01F 6/62 | (2006.01) |
| C01B 32/50 | (2017.01) |
| B05D 7/00 | (2006.01) |
| B05D 1/18 | (2006.01) |
| B05D 1/36 | (2006.01) |

(52) U.S. Cl.
CPC .............. *B82Y 30/00* (2013.01); *C01B 32/50* (2017.08); *D01F 6/625* (2013.01); *B01J 2231/70* (2013.01); *B05D 1/185* (2013.01); *B05D 1/36* (2013.01); *B05D 7/52* (2013.01); *B05D 7/56* (2013.01); *B32B 2262/0276* (2013.01); *B32B 2307/402* (2013.01); *B32B 2457/00* (2013.01)

(56) References Cited

U.S. PATENT DOCUMENTS

| | | | |
|---|---|---|---|
| 2004/0203071 A1 | 10/2004 | Chase | |
| 2005/0175507 A1* | 8/2005 | Tsukruk | B01D 67/0069 422/68.1 |
| 2005/0208100 A1* | 9/2005 | Weber | A61L 27/34 424/426 |
| 2006/0029808 A1* | 2/2006 | Zhai | B05D 5/04 428/412 |
| 2010/0098902 A1 | 4/2010 | Kotov | |
| 2011/0064936 A1 | 3/2011 | Hammond-Cunningham | |
| 2012/0058697 A1 | 3/2012 | Strickland | |
| 2014/0026714 A1* | 1/2014 | Murphy | B22F 1/0025 75/370 |

OTHER PUBLICATIONS

Correa-Duarte, M., et al., "Aligning au nanorods by using carbon nanotubes as templates," 2005, pp. 4375-4378, vol. 44, Angewandte Chemie Int. Ed.

Crane, L., et al., "SERS surfaces modified with a 4-(2-Pyridylazo) resorcinol disulfide derivative: detection of copper, lead, and cadmium," Jan. 15, 1995, pp. 360-364, vol. 67, No. 2, Analytical Chemistry.

Gole, A., et al., "Polyelectrolyte-coated gold nanorods: synthesis, characterization and immobilization," Feb. 9, 2005, pp. 1325-1330, vol. 17, No. 6, Chemistry of Materials.

Gorelikov, I., et al., "Hybrid microgels photoresponsive in the near-infrared spectral range," Nov. 16, 2004, pp. 15938-15939, vol. 126, No. 49, Journal of American Chemical Society.

Hu, X., et al., "Fabrication, characterization, and application in SERS of self-assembled polyelectrolyte—gold nanorod multilayered films," Sep. 22, 2005, pp. 19385-19389, vol. 109, No. 41, The Journal of Physical Chemistry B.

International Search Report and Written Opinion for International Application No. PCT/US2014/023994 dated Jun. 27, 2014.

Kuncicky, D., et al., "Controlled assembly of SERS substrates templated by colloidal crystal films," 2006, pp. 1207-1211, vol. 16, Journal of Materials Chemistry.

Lee, C.H., et al., "Directed assembly of gold nanorods using aligned electrospun polymer nanofibers for highly efficient SERS substrates," 2011, pp. 1-8, vol. 22, Nanotechnology.

Sau, T.K., et al., "Seeded high yield synthesis of short au nanorods in aqueous solution," Jun. 19, 2004, pp. 6414-6420, vol. 20, No. 15, Langmuir.

Tang, W., et al., "Immobilization of gold nanorods onto electrospun polycaprolactone fibers via polyelectrolyte decoration—a 3D SERS substrate," Oct. 2013, pp. 10702-10709, vol. 85, No. 22, Analytical Chemistry.

Tessier, P.M., et al., "Assembly of gold nanostructured films templated by colloidal crystals and use in surface-enhanced raman spectroscopy," Sep. 16, 2000, pp. 9554-9555, vol. 122, No. 39, Journal of the American Chemical Society.

Vial, S., et al., "Plasmon coupling in layer-by-layer assembled gold nanorod films," Mar. 17, 2007, pp. 4606-4611, vol. 23, No. 8, Langmuir.

Wang, C., et al., "Monodispersed gold nanorod-embedded silica particles as novel raman labels for biosensing," 2008, pp. 355-361, vol. 18, Advanced Functional Materials.

Yuan, Y., et al., "Surface enhanced Raman spectroscopic readout on heavy metal ions based on surface self assembly," Jun. 11, 2007, pp. 1280-1287, vol. 38, Journal of Raman Spectroscopy.

Zamarion, V., et al., "Ultrasensitive SERS nanoprobes for hazardous metal ions based on trimercaptotriazine-modified gold nanoparticles," Mar. 26, 2008, pp. 2934-2936, vol. 47, No. 8, Inorganic Chemistry.

* cited by examiner

GOLD NANOROD/POLYMER NANOCOMPOSITES AND SENSORS BASED THEREON

CROSS-REFERENCE TO RELATED APPLICATION

This application is the National Phase filing of International Patent Appln. No. PCT/US2014/023994, filed Mar. 12, 2014, and claims the priority benefit of U.S. Provisional Application No. 61/781,064 filed Mar. 14, 2013, the contents of which applications are incorporated herein by reference in their entireties for all purposes.

This invention was made with government support under Contract Nos. DMR-0704970, DMR-0643226, and Delaware EPSCoR-1301765 awarded by the National Science Foundation. The government has certain rights in the invention.

BACKGROUND OF THE INVENTION

Metallic nanoparticles (MNPs) have generated extensive research interest during the past few decades due to their fascinating optical, electronic and catalytic properties. Since the properties of MNPs are size and shape dependent, significant research efforts have been devoted to the controlled synthesis of MNPs with anisotropic geometries, such as gold nanorods (AuNRs). Due to the geometrical change, AuNRs exhibit substantially different properties compared to spherical gold nanoparticles, one of which is their plasmonic properties. Unlike spherical gold nanoparticles, which give rise to one single surface plasmon resonance (SPR) band in the extinction spectrum, the SPR for AuNRs splits into two modes. The electron oscillation along the short axis and long axis of the nanorods results in the appearance of a transverse SPR band and a much stronger longitudinal SPR band, respectively. Besides the strong light adsorption, the longitudinal SPR band of the AuNRs can be effectively tuned from the visible to the near-infrared region, facilitating easy coupling to commercial laser sources. Thus, AuNRs have become very promising building blocks for surface enhanced Raman scattering (SERS) substrates.

One critical feature of an effective SERS substrate is the presence of 'hot spots' arising from the plasmon coupling between closely packed metallic nanostructures. Various techniques have been used to produce such highly dense nanorod assemblies, including solvent evaporation, Langmuir-Blodgett assembly, assembly driven by the interaction between the capping molecules on nanorod surfaces, assembly at a liquid-liquid interface, etc. Unfortunately, the applicability of these approaches has generally been limited to two-dimensional (2D) planar substrates, i.e., sheet-like substrates. For sensing applications, however, three-dimensional (3D) substrates with hierarchical structures (e.g., fibrous meshes, micro- or nanosphere aggregates etc.) are preferred due to the enhanced surface area, which leads to better detection. To produce MNP assemblies on 3D structures, substrates carrying metal-affinitive functional groups (e.g., thiol groups, pyridyl groups, etc.) have generally been used, and the exclusive chemistry occurring between the MNPs and the substrate provides the driving force for MNP immobilization. Since this type of MNP immobilization relies on the formation of specific chemical bonds, application of such methods is confined to a limited range of substrate materials. Thus, the ability to immobilize MNP on 3D substrates made from a variety of materials would be a welcome addition to the art.

SUMMARY OF THE INVENTION

In some aspects, the invention provides a nanocomposite structure including:

a) a charged fibrous substrate including fibers having disposed on their surfaces a multilayer structure including a layer of a first polyelectrolyte and disposed thereon a layer of a second polyelectrolyte of opposite charge from the first, the second polyelectrolyte forming the outermost layer of the charged fibrous substrate; and b) charged nanorods having a charge opposite that of the charged fibrous substrate, including gold nanorods each having disposed on its surface one or more layers, the outermost of which is a third polyelectrolyte having a charge opposite that of the second polyelectrolyte, wherein the first and third polyelectrolytes may be the same or different;

wherein the charged nanorods are disposed unaligned with respect to each other on the charged fibrous substrate.

In some aspects, the invention provides a method of analyzing for a chemical species, including contacting the nanocomposite structure with a fluid including the chemical species to bind the chemical species to the nanocomposite structure, and performing surface enhanced Raman spectroscopy on the nanocomposite structure with the bound chemical species.

In some aspects, the invention provides a method of making a nanocomposite structure, including a) providing alternating layers of cationic and anionic polyelectrolytes on the fibers of a fibrous substrate to produce a charged fibrous substrate, the charge of which is defined by the last layer of polyelectrolyte;

b) applying one or more charged layers to gold nanorods, the outermost layer having a charge opposite that of the charged fibrous substrate; and c) contacting the charged fibrous substrate with the nanorods prepared in step b).

DETAILED DESCRIPTION OF THE INVENTION

The invention provides effective fabrication of a 3D substrate comprising AuNR nanorods disposed on the surface of the fibers of a fibrous substrate, using non-specific electrostatic attraction to irreversibly bind the AuNRs onto the fibers. Typically, uniform surface coverage of AuNRs on the fibers is obtained, as viewed by scanning electron microscopy. Generally, all of the AuNRs are on the surface of the self-supporting fibers that compose the fibrous substrate, and no AuNRs are embedded in those fibers or in any self-supporting film-like or other self-supporting structure forming a part of, or admixed with, the fibrous substrate.

The fibrous substrate will typically be a woven or nonwoven substrate, and suitable ones may be any of a variety of shapes and materials made by any known process. In some embodiments, the substrate is produced by electrospinning, although other techniques may be used. For simplicity, the bulk of the description herein will relate to use of an electrospun polycaprolactone (PCL) fibrous mesh as the substrate, but it is to be understood that any fibrous substrate is suitable and contemplated for use according to the invention. Exemplary materials include dielectric materials, for example polymers and glasses, but metals and other conductive materials may also be used. All of the statements made herein regarding embodiments of the invention are to be understood to apply to AuNR assemblies on any fibrous substrate, unless the context indicates otherwise.

Opposite charges are first established on the AuNRs and the PCL fibers via deposition of oppositely charged polyelectrolytes on each. In some embodiments, this will cause the substrate to carry a positive charge and the AuNRs a negative charge, although the reverse can be used. Typically, layer by layer (LBL) deposition will be used to produce the charge on the substrate, in which at least one layer of anionic polyelectrolyte and at least one layer of cationic polyelectrolyte is deposited. Many alternating layers of cationic polyelectrolyte and anionic polyelectrolyte may be used, and neither the cationic nor the anionic polyelectrolyte layers need all be of the same composition. One suitable cationic polyelectrolyte is poly(diallyldimethylammonium chloride) (PDADMAC), and one suitable anionic polyelectrolyte is poly(sodium 4-styrenesulfonate) (PSS). However, any cationic polyelectrolyte and/or anionic polyelectrolyte can be used according to the invention.

Subject to the requirement that layers alternate in charge, the total number of anionic layers will typically be an integer from 1 to 10, inclusive, and the total number of cationic layers will typically be an integer from 1 to 10, inclusive. More can be used, however. The charge on the final layer determines the charge on the substrate.

Gold nanorods in some embodiments of the invention have a length of at least 10 nm, or at least 20 nm, or at least 30 nm, and at most 65 nm, or at most 55 nm, or at most 45 nm. However, larger nanorods can be used in some embodiments, including up to 1000 nm, or up to 900 nm, or up to 800 nm, or up to 700 nm, or up to 600 nm, or up to 500 nm, or up to 400 nm, or up to 300 nm, or up to 200 nm, or up to 100 nm. They typically have an aspect ratio of at least 2:1, or at least 2.5:1, or at least 2.8:1. The aspect ratio is typically at most to 5:1, or at most to 4:1, or at most to 3.5:1, or at most to 3.2:1. In the case where the charge on the substrate is positive, immobilization of AuNRs is initiated by immersing the charged substrate in a solution of negatively charged colloidal AuNRs. The charged AuNRs may be prepared by applying one or more charged layers to the AuNRs. In one embodiment, they are made by contacting cationically stabilized gold nanorods, for example stabilized with hexadecyltrimethylammonium bromide (CTAB) or another cationic surfactant or a layer of cationic polyelectrolyte, with an anionic polyelectrolyte, for example poly(sodium 4-styrenesulfonate (PSS). With the proper immersion time, a homogeneous and highly dense AuNR deposition is produced on the PCL fiber surface.

The resulting AuNR/PCL nanocomposite serves as an effective SERS substrate that detects chemisorbed or electrostatically bound molecules with excellent reproducibility, in some cases at solution concentrations of the target molecule as low as $10^{-7}$M. Due to the non-specific nature of the electrostatic interaction binding the AuNR to the fibrous substrate, the fabrication protocol demonstrated in this work is suitable for production of nanocomposite materials with various compositions and morphologies.

Examples

All the chemicals were purchased from Sigma-Aldrich and used as received unless otherwise specified.
Preparation of Negatively Charged Gold Nanorods AuNRs were synthesized using the seed-mediated growth protocol as has been reported in the literature. Briefly, hexadecyltrimethylammonium bromide (CTAB) stabilized gold nanoparticles were produced by adding 0.6 mL of freshly prepared 0.01M ice-cold $NaBH_4$ solution to a mixture containing 7.5 mL of 0.1M CTAB and 0.25 mL of 0.01M $HAuCl_4$. The resulting solution contained the seeds for the growth of AuNRs in the following steps and was stored for over 2 hrs before further use. Subsequently, 0.2 mL of 0.01M $HAuCl_4$, 0.03 mL of 0.01M $AgNO_3$ and 0.032 mL of 0.1M ascorbic acid were added to 4.75 mL of 0.1M CTAB solution in the order stated. Finally, 0.01 mL seed solution was added to initiate the growth of AuNRs. A color change of the solution from clear to dark purple occurred during the next ten minutes, suggesting the formation of AuNRs. The AuNR solution was stored overnight to allow for full growth of the AuNRs.

The nanorods were characterized using transmission electron microscopy (TEM, JEOL JEM-2000FX, 200 kV accelerating voltage) and UV-Vis spectroscopy (Shimadzu UV-3600 UV-VIS-NIR spectrophotometer) before further use. The as-synthesized AuNRs were estimated to be 37.3±7.6 nm in length and 12.1±1.9 nm in width (Average aspect ratio ~3), exhibiting the transverse SPR absorbance at 521 nm and the longitudinal SPR absorbance at 786 nm, respectively.

Theoretically, the CTAB stabilized gold nanorods, which carry net positive charges in solution, can be readily immobilized onto a negatively charged surface. However, one critical feature of an effective SERS substrate is the presence of 'hot spots', which usually exist at the junction of densely packed nanorod assemblies. To encourage denser AuNR deposition, a poly(sodium 4-styrenesulfonate) (PSS) layer was deposited onto the as-synthesized CTAB stabilized AuNRs, increasing their zeta potential.

In a typical procedure, aliquots of the as-synthesized AuNR solution were transferred into 2 mL microcentrifuge tubes and centrifuged at 13,000 rpm for 12 mins. The precipitates from each tube were then re-dispersed in 0.75 mL of 2 mg/mL PSS solution. The ionic strength of the PSS solution was previously adjusted to 1 mM by the addition of NaCl (99%+, ACROS). The re-dispersed AuNR solutions were left undisturbed for 1 hr to allow for PSS adsorption. Thereafter, the solutions were centrifuged twice at 13,000 rpm for 12 mins to wash off the excess PSS. The final precipitates were re-dispersed in deionized (DI) water (18.2 MΩ·cm, Millipore Co.) with a AuNR concentration that was ⅔ of its original concentration.

To demonstrate the decoration of PSS onto the AuNRs, attenuated total reflection Fourier transform infrared spectroscopy (ATR-FTIR) measurements were carried out on a Nexus 670 FTIR instrument (Thermo Nicolet) with a PIKE MIRacle ATR accessory. All the ATR-FTIR spectra were recorded with 4 $cm^{-1}$ resolution.

Figure 1:
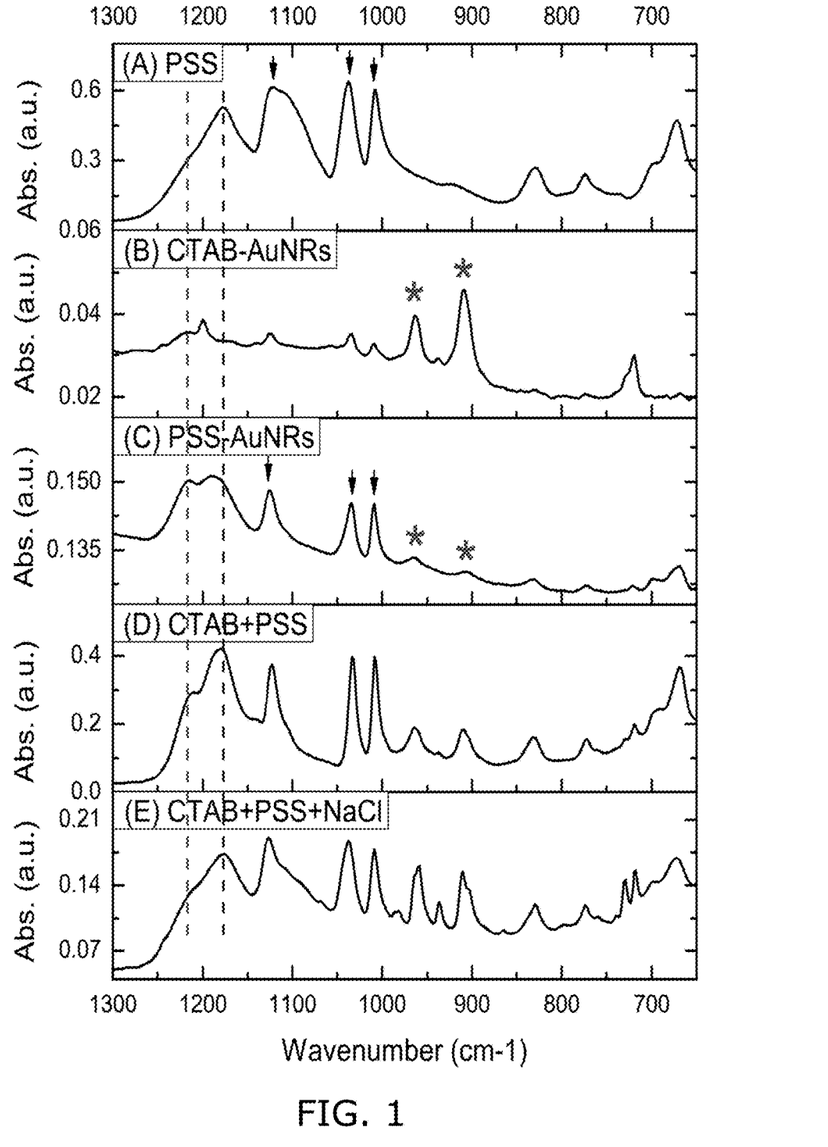
FIG. 1 shows ATR-FTIR spectra of (A) pure poly(sodium 4-styrenesulfonate (PSS), (B) as-synthesized CTAB stabilized AuNRs (CTAB-AuNRs), (C) PSS decorated AuNRs (PSS-AuNRs), (D) a CTAB+PSS complex and (E) a CTAB/PSS mixture with the presence of salt (CTAB+PSS+NaCl).

FIG. 1 shows ATR-FTIR spectra of (A) pure PSS, (B) the as-synthesized CTAB stabilized AuNRs (CTAB-AuNRs), (C) the PSS decorated AuNRs (PSS-AuNRs), (D) the CTAB+PSS complex and (E) the CTAB/PSS mixture with the presence of salt (CTAB+PSS+NaCl).

A comparison between the spectra of CTAB-AuNRs and PSS-AuNRs indicates that the two most intense peaks at around 964 and 908 $cm^{-1}$ (labeled by the asterisks) in the spectrum of CTAB-AuNRs, which arise from the vibration of the C—$N^+$ groups in the CTAB bilayer on the AuNR surface, show up at the same position in the spectrum of PSS-AuNRs. In addition, the peaks at around 1124, 1034 and 1009 $cm^{-1}$ (labeled by the arrows) in the spectrum of PSS-AuNRs also match nicely with those specific peaks from PSS. Besides the perfectly matched peaks, two distinct spectral features in the spectrum of PSS-AuNRs are seen. First, a new peak shows up at 1215 $cm^{-1}$ (marked by the dashed line on the left) in the spectrum of the PSS-AuNRs, which cannot be simply attributed to either PSS or CTAB-AuNRs. Second, the peak at around 1178 $cm^{-1}$ in pure PSS has shifted to 1188 $cm^{-1}$ in the spectrum of PSS-AuNRs, marked by the dashed line on the right.

With the deposition of a PSS layer onto the CTAB-AuNRs, a likely interaction would be electrostatic attraction between the sulfonate anions in PSS and the quaternary ammonium cations in CTAB. Therefore, the ATR-FTIR spectrum of the CTAB+PSS complex was recorded and is shown in FIG. 1D. The CTAB+PSS complex was produced by mixing the CTAB solution with the PSS solution at a molar ratio of 1:1. The precipitates were collected and their spectra were recorded. By comparison, the matching peak for the new peak at 1215 $cm^{-1}$ is found in the spectrum of CTAB+PSS complex, which suggests that this new peak most likely arises due to electrostatic interactions. To further validate this assumption, the spectrum of the CTAB/PSS mixture with the presence of an extensive amount of salt (CTAB+PSS+NaCl) was acquired and is shown in FIG. 1E. The salt was added to screen the electrostatic interaction between the two oppositely charged species. From the three spectra shown in FIG. 1 panels C, D and E, the new peak at 1215 $cm^{-1}$ appears with the presence of electrostatic interaction and disappears with its absence. This indicates that this peak originates from the electrostatic interaction between the PSS and the CTAB bilayer on the AuNR surface. In addition, a comparison among the three spectra shown in FIGS. 1C, D, and E shows that there is no shift in the peak at 1178 $cm^{-1}$ upon CTAB+PSS complexation. Since the peak at 1178 $cm^{-1}$ arises from the antisymmetric vibration of the sulfonate groups in PSS, the shift observed in the spectrum of PSS-AuNRs most likely originates from the interaction between the sulfonate groups with the AuNRs. The presence of all the above mentioned features in the spectrum of PSS-AuNRs provides strong evidence of the successful deposition of PSS onto the CTAB-AuNRs with electrostatic interactions between PSS and both the CTAB bilayer and the AuNR itself.

Preparation of PCL Fibrous Substrates

PCL fibrous mesh substrates were produced by electrospinning on a conventional setup. Generally, a syringe loaded with the 25% wt/v PCL/chloroform solution was mounted on a syringe pump (NE-300, New Era Pump Systems Inc.) to guarantee a constant flow rate of 0.5 mL/hr. A piece of aluminum foil was placed 25 cm away from the tip of the needle and used to collect the fibers. A Spellman power supply (CZE1000R, SPELLMAN) was employed to apply a potential difference between the needle and the collector (+12 kV and −3 kV, respectively).

Positively Charging the PCL Fibrous Substrates

To develop the positive charges on the substrate, polyelectrolyte LBL deposition technique was utilized. Briefly, polyelectrolyte multilayers were deposited onto PCL mesh by the alternate immersion of PCL mesh into poly(diallyldimethylammonium chloride) (PDADMAC) solution (3 mg/mL) and PSS solution (3 mg/mL) with washing steps in between. The ionic strength of the polyelectrolyte solutions was adjusted to 1M by the addition of NaCl and the deposition cycle was repeated several times until the desired number of polyelectrolyte layers had been deposited.

ATR-FTIR measurements were carried out to study the polyelectrolyte multilayer deposition process. The ATR-FTIR spectra of PSS, pristine PCL mesh and PCL meshes coated with various numbers of polyelectrolyte layers were recorded with 4 $cm^{-1}$ resolution.

Figure 2:
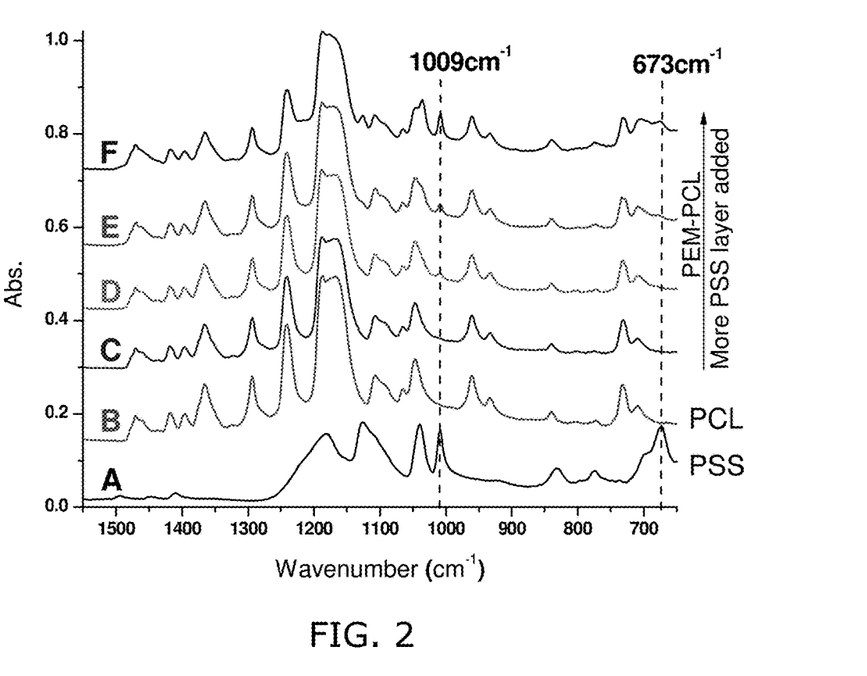
FIG. 2 shows ATR-FTIR spectra of (A) pure PSS, (B) pristine polycaprolactone (PCL) mesh and PCL meshes decorated with various numbers of polyelectrolyte multilayers: (C) PCL-(PDADMAC/PSS)$_1$, (D) PCL-(PDADMAC/PSS)$_{2.5}$, (E) PCL-(PDADMAC/PSS)$_{3.5}$ and (F) PCL-(PDADMAC/PSS)$_{5.5}$. The number N in the nomenclature PCL-(PDADMAC/PSS)$_N$ denotes the number of PDADMAC/PSS bilayers deposited on the PCL mesh.

FIG. 2 shows ATR-FTIR spectra of (A) pure PSS, (B) pristine PCL mesh and PCL meshes decorated with various numbers of polyelectrolyte multilayers: (C) PCL-(PDADMAC/PSS)$_1$, (D) PCL-(PDADMAC/PSS)$_{2.5}$, (E) PCL-(PDADMAC/PSS)$_{3.5}$ and (F) PCL-(PDADMAC/PSS)$_{5.5}$. The number N in the nomenclature PCL-(PDADMAC/PSS)$_N$ denotes the number of PDADMAC/PSS bilayers deposited on the PCL mesh.

Referring to the ATR-FTIR spectra of pristine PCL and PSS in FIG. 2 spectra A and B, the peaks in the spectrum of PSS at 1009 $cm^{-1}$ and 673 $cm^{-1}$ are chosen as the indicators to study the deposition of polyelectrolyte layers, because those two peaks arise from the benzene ring structure exclusively existing in PSS and they show up at positions where there is no overlap with the signals from PCL, making the spectra easier to analyze. As shown in FIG. 2 spectra C to F, the peak at 1009 $cm^{-1}$ begins to appear after 2 layers of PSS have been deposited and it becomes more evident as more PSS layers are added. Similarly, the peak at 673 cm$^{-1}$ first shows up as a shoulder and gradually develops into an easily distinguishable peak. These observations strongly indicate successful deposition of the polyelectrolyte multilayer. More direct evidence of the presence of polyelectrolyte multilayer on the PCL fiber surface was provided by an XPS survey spectrum recorded on the PCL-(PADAMAC/PSS)$_{5.5}$ mesh (not shown). Detection of sulfur and nitrogen, which exist exclusively in PSS and PDADMAC, respectively, further confirmed the successful deposition of the polyelectrolyte multilayer.

Effect of Number of Polyelectrolyte Deposition Cycles

In the present work, it was found that for a neutral substrate like PCL fibers, only partial polyelectrolyte coverage could be achieved with the first few cycles of polyelectrolyte deposition, due to the lack of anchoring sites for the initial polyelectrolyte layer. Water contact angle (WCA) measurements were therefore used to assess completeness of polyelectrolyte coverage.

Figure 3:
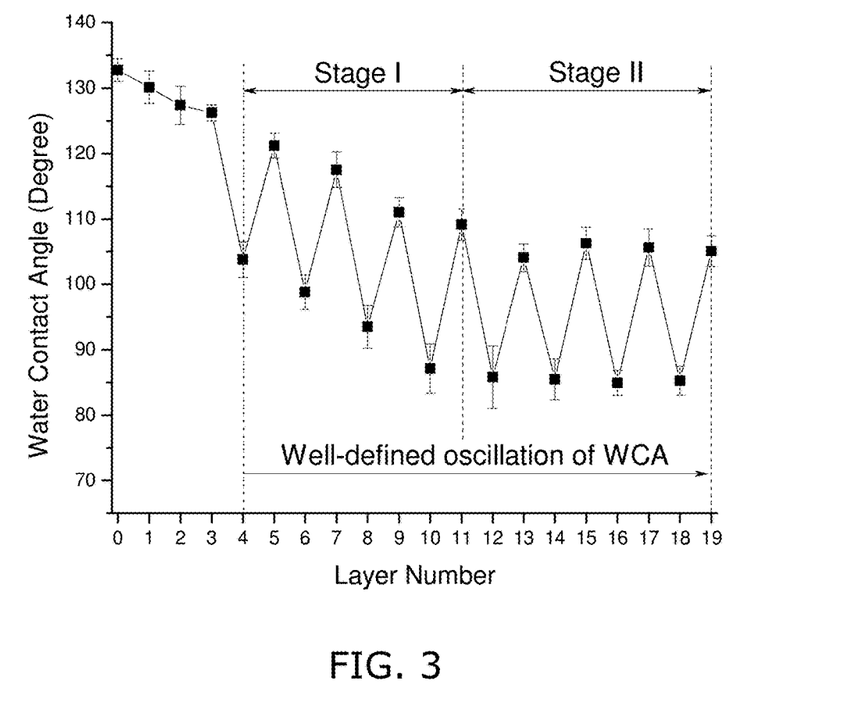
FIG. 3 shows the change in water contact angle with the layer by layer deposition of polyelectrolyte layers.

The change of WCA with the number of deposited polyelectrolyte layers is shown in FIG. 3. Layer 0 corresponds to the pristine PCL fibrous substrate without polyelectrolyte coating, and the measured WCA value is approximately 133 degrees. The odd numbered layers correspond to the PDADMAC terminated layers and the even numbered layers correspond to the PSS terminated layers, respectively. The WCA begins to decrease upon deposition of the polyelectrolyte layers due to the more hydrophilic nature of the polyelectrolytes. In addition, the PDADMAC terminated layers always exhibit higher WCA values than the PSS terminated layers, indicating a higher hydrophobicity of PDADMAC. From FIG. 3, the starting point of well-defined oscillation of the WCA with the deposition of polyelectrolytes, which suggests the formation of complete surface coverage, was determined to be layer 4. However, since the PSS-AuNRs carry net negative charges, immobilization driven by electrostatic attraction requires the substrate to be positively charged. Thus, in this system the preferred minimum number of polyelectrolyte layers was 5.

Furthermore, the zigzag trend of the measured WCAs can be divided into two stages, as labeled in FIG. 3. In stage I, a decreasing trend of WCAs measured on both the odd and even numbered layers has been observed. When entering stage II, the WCAs begin to stabilize at two distinct levels, around 105 degrees for the PDADMAC terminated layers and 85 degrees for the PSS terminated layers, respectively. Without wishing to be bound by any theory or explanation, the inventors believe that stage II marks the point at which fibers' pores and/or other surface roughness features, which increase WCA, have been smoothed over by the deposited layers.

Immobilization of Gold Nanorods on PCL Fibrous Substrates

The polyelectrolyte multilayer decorated PCL mesh (PEM-PCL) was cut into small pieces, each with a size of approximately 1 cm$^2$. One of the pieces was subsequently immersed in 9 mL of the PSS decorated AuNR (PSS-AuNR) solution for 24 hrs. During this time, the color of the fibrous substrate changed from white to dark purple, resembling the color of the AuNR colloidal solution. Afterwards, the PEM-PCL mesh was taken out from the PSS-AuNR colloidal solution and washed with DI water to remove any loosely bound AuNRs. The resulting AuNR/PCL nanocomposite mesh was left to dry under ambient condition before further use.

Figure 4:
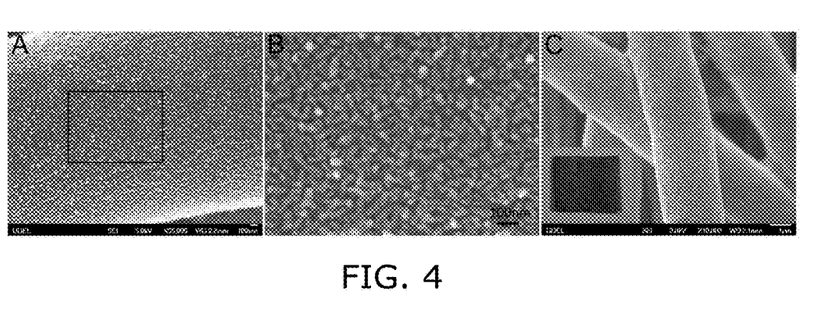
FIG. 4 panels A-C show SEM images of AuNR/PCL nanocomposite fibers according to the invention. Panel A was recorded at a magnification of 35K. Panel B is an enlarged image of the rectangular area in panel A. Panel C was recorded at a magnification of 10K. Inset: A digital photograph of the AuNR-PCL nanocomposite mesh.

FIG. 4 shows scanning electron microscopy (SEM) images of the AuNR/PCL nanocomposite mesh, (A) Recorded at a magnification of 35K, (B) Enlarged image of the rectangular area in (A), and (C) Recorded at a magnification of 10K. Inset: A digital photograph of the AuNR-PCL nanocomposite mesh. The uniform shading/coloration of the substrate indicates the formation of a uniform AuNR assembly throughout the whole mesh. In addition, on each single PCL fiber, a homogenous AuNR coating was produced with the particles showing essentially no aggregation and no apparent alignment with or against the long axis of the fibers, or circumferentially around the fibers, or relative to each other, as shown in FIG. 4 panels A and B. These features are typical of AuNR assemblies on the surface of the fibers of a fibrous substrate according to the invention. Typically, the AuNRs do not form stripes, lines, chainlike structures or other organized features or assemblies among themselves. Rather, the AuNRs are typically disposed unaligned with respect to each other on the surface of the fiber. Their orientation is typically random with respect to each other. Their number density is typically sufficient to provide a AuNR particle density high enough to provide full surface coverage of the fibers. In many cases, a nanorod will be within a distance less than its own length from anther nanorod. In some embodiments, at least 25% by number, or more than 50% by number, of nanorods are within such a distance.

Attachment of SERS Probes to Immobilized Gold Nanorods 4-mercaptopyridine (4-MPy) and Rhodamine 6G (Rh6G) were used as probe molecules. To prepare the samples bearing adsorbed 4-MPy, six pieces of AuNR/PCL nanocomposite mesh were soaked in 7 mL of 4-MPy/ethanol solutions with varying concentrations (from $10^{-3}$M to $10^{-7}$M) for 2 hrs. Afterwards, the meshes were washed first with ethanol and then DI water to remove any loosely bound 4-MPy molecules. The substrates were left to dry under reduced pressure before SERS measurements. In addition, for a negative control, a sample was fabricated by soaking a piece of PEM-PCL mesh in 7 mL of 5×$10^{-3}$M 4-MPy/ethanol solution for 2 hrs. Similar procedures were carried out to prepare the Rh6G samples.

SERS Evaluation

The performance of the resulting AuNR/PCL nanocomposite fibers as a SERS substrate was first investigated using 4-mercaptopyridine (4-MPy) as the probe molecule. This choice was made based on the distinctive Raman spectral features of 4-MPy and its effective binding to AuNR surface via the thiol groups.

SERS measurements were performed on a Raman instrument that was composed of an Invictus diode laser with 785 nm excitation and a Kaiser Optical Systems, Inc. (Ann Arbor, Mich.) Holospec VPT System. The laser power was two milliwatts at the sample surface, and all the SERS spectra were collected using a 30 s exposure time.

Figure 5:
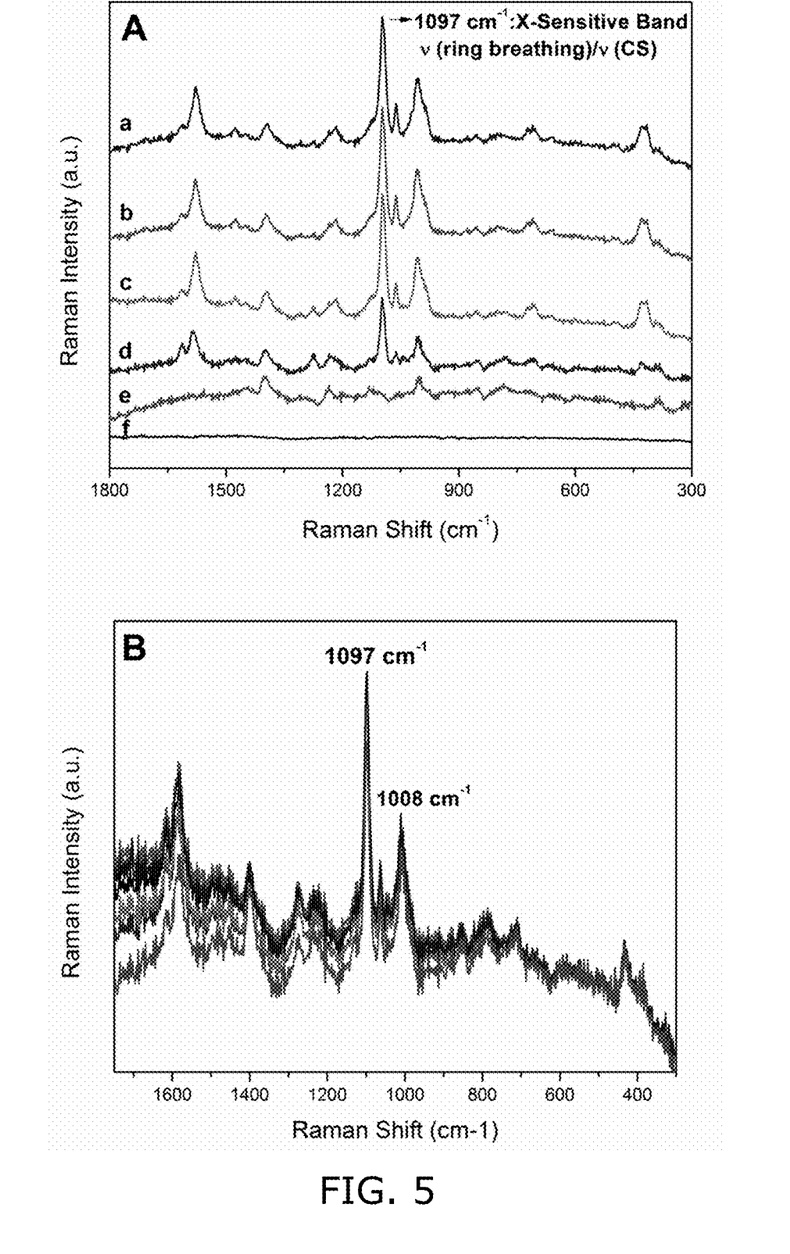
FIG. 5 panel A shows SERS spectra of 4-mercaptopyridine (4-MPy) recorded on AuNR/PCL nanocomposite fibers according to the invention at various probe molecule concentrations: (a) $10^{-3}$M, (b) $10^{-4}$M, (c) $10^{-5}$M, (d) $10^{-6}$M, (e) $10^{-7}$M and (f) control experiment—$5\times10^{-3}$M 4-MPy on PEM-PCL mesh. Panel B shows SERS spectra of $10^{-6}$ M 4-MPy recorded on seven randomly selected spots on an AuNR/PCL nanocomposite mesh according to the invention.

The SERS spectra shown in Figure panel A were recorded at varied probe molecule concentrations, ranging from $10^{-3}$ to $10^{-7}$M. As shown in Figure panel A, the SERS intensity remains almost unchanged as the probe molecule concentration decreases from $10^{-3}$M to $10^{-5}$M and begins to level off as the concentration further decreases, which indicates the saturation concentration is between $10^{-6}$M and $10^{-5}$M. Furthermore, the as-fabricated AuNR/PCL nanocomposite fibers can detect as low as $10^{-7}$M 4-MPy in solution.

The reproducibility of the SERS measurements was also investigated by collecting a series of spectra on seven randomly selected spots on the nanocomposite fibers. The spectra are shown in FIG. 5 panel B. The average intensities of the two peaks at 1097 cm$^{-1}$ and 1008 cm$^{-1}$ were calculated to be 1576±72 (Relative Standard Deviation, RSD~4.57%) and 749±37 (RSD~4.94%), respectively. The intensity variations of both two peaks are less than 5%, indicating an excellent reproducibility of the SERS results. The high reproducibility further confirms the production of a homogeneous AuNR assembly on the PCL fibers.

Comparison of SERS Intensity on Fibrous vs. Planar Substrate

Since the SERS substrate fabricated in the present work is constructed by immobilizing the AuNRs onto a 3D fibrous mesh, it has the advantage of enhanced surface area compared to the traditional 2D planar SERS substrates. The effect of enhanced surface area on the SERS performance was assessed by comparing the SERS response of the 3D AuNR/PCL fibrous mesh to its 2D planar counterpart, an AuNR/PCL film. The AuNR/PCL film was fabricated using the same procedures as the AuNR/PCL fibers except that the initial substrate was a smooth PCL film instead of a PCL fibrous mesh. The AuNR/PCL film was characterized by SEM before further use and the photos are shown in FIG. 6.

Figure 6:
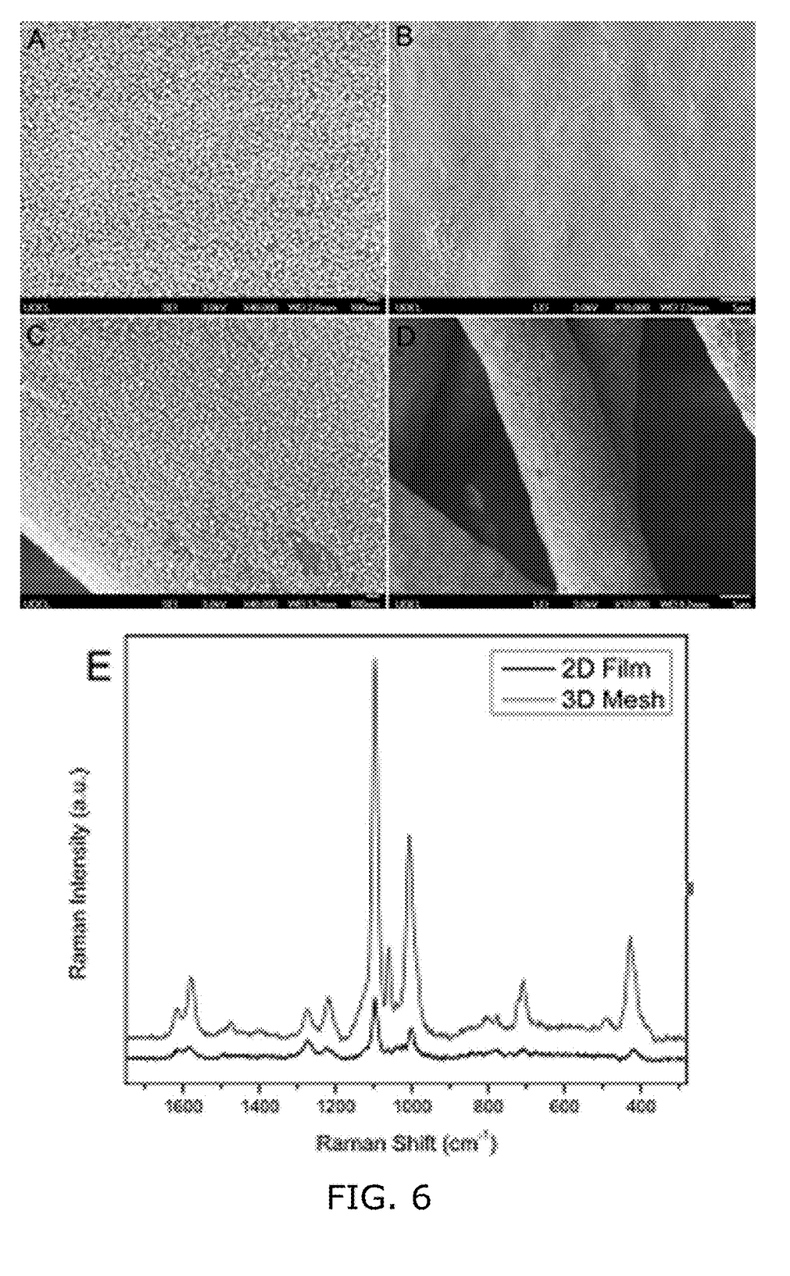
FIG. 6 panels A and B are SEM images of AuNR/PCL film taken under magnifications of 40K and 10K. Panels C and D are SEM images of AuNR/PCL fibers according to the invention taken under magnifications of 40K and 10K. Panel E shows SERS spectra of 1 mM 4-MPy recorded on the 2D and 3D SERS substrates with an acquisition time of 30 s.

FIG. 6 panels A and B are SEM images of AuNR/PCL film taken under magnifications of 40K and 10K. Panels C and D are SEM images of AuNR/PCL fibers taken under magnifications of 40K and 10K. Panel E shows SERS spectra of 1 mM 4-MPy recorded on the planar (2D) and 3D SERS substrates with an acquisition time of 30 s, showing considerable enhancement using the 3D (i.e., fibrous) substrate.

As can be seen, the density of AuNRs on the 2D planar film is similar to the 3D mesh. The concentration of 4-MPy is chosen at 1 mM, which is well-above the saturation concentration. Under those conditions, the SERS intensity recorded on the 3D mesh is over 6-fold of the intensity obtained on the 2D planar film, as shown in FIG. 6 panel E.

Figure 7:
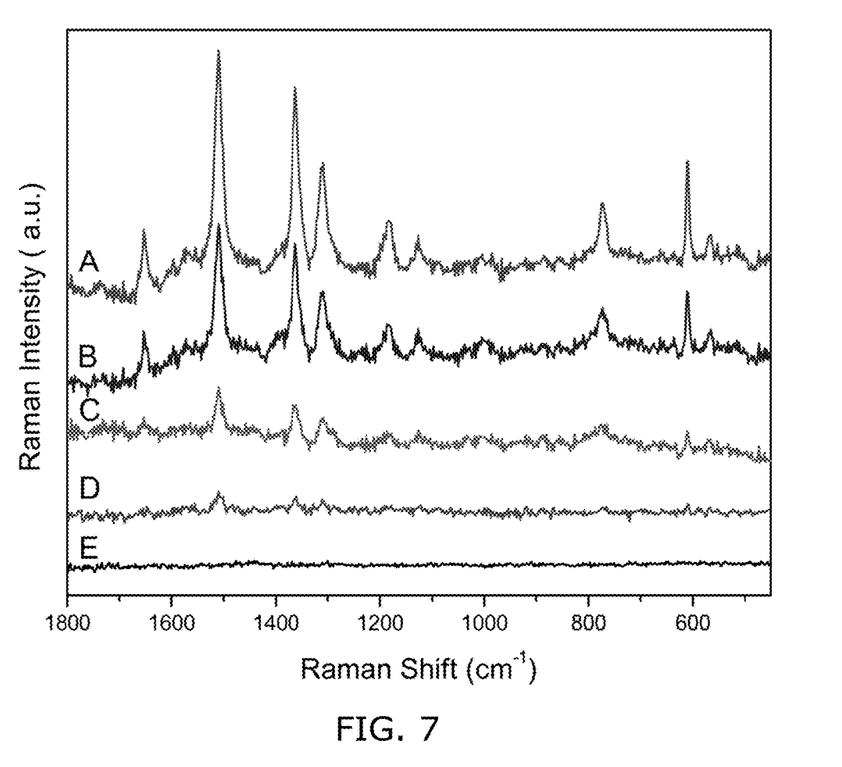
FIG. 7 shows SERS spectra of Rhodamine 6G (Rh6G) recorded on AuNR/PCL nanocomposite fibrous mesh according to the invention at various probe molecule concentrations: A) $10^{-4}$ M, B) $10^{-5}$ M, C) $10^{-6}$ M, D) $10^{-7}$ M and E) control experiment $-10^{-3}$ M Rh6G on PEM-PCL fibrous mesh.

SERS detection of another common Raman probe molecule, Rhodamine 6G (Rh6G), was also conducted. Rh6G is a cationic dye that carries positive charge upon dissociation, allowing the Rh6G molecules to electrostatically bind to the negatively charged PSS-AuNRs on the PCL fiber surface. FIG. 7 shows the SERS spectra of Rh6G recorded at various probe molecule concentrations: A) $10^{-4}$ M, B) $10^{-5}$ M, C) $10^{-6}$ M, D) $10^{-7}$ M and E) control experiment—$10^{-3}$ M Rh6G on PEM-PCL fibrous mesh. The effective binding facilitated by electrostatic attraction allows the detection of as low as $10^{-7}$M Rh6G under the non-resonant conditions.

Attachment of Bridging Molecules to Immobilized Gold Nanorods

Bridging molecules capable of interacting with and/or binding metal ions can be attached to immobilized gold nanorods in a manner analogous to that described above for attaching SER probes. Each of the bridging molecules comprises a moiety capable of binding to the gold nanorods and a moiety capable of binding to a metal ion. In some embodiments, the moiety capable of binding to the gold nanorods comprises a mercapto (SH) group. Another example is a pyridyl group. In some embodiments, the moiety capable of binding to a metal ion comprises a COOH group, for example a moiety from an aromatic carboxylic acid such as benzoic acid moiety or a moiety from a heteroaromatic carboxylic acid such as a nicotinic acid moiety, or a triazine group, or a chelating group such as an EDTA moiety. The choice of moiety depends upon the metal ion, and suitable moieties for a given metal will be apparent to the skilled person.

The metal ions can for example be transition metal ions. In some embodiments, the bridging molecule interacts and/or binds with heavy metal ions, for example $Cu^{2+}$, $Hg^{2+}$, $Pb^{2+}$, and $Cd^{2+}$. Examples of bridging molecules include 4-mercaptobenzoic acid, 2-mercaptonicotinic acid and 2,4,6-trimercapto-1,3,5-triazine. These interact with and bind to AuNRs via the mercapto groups, while other functional moieties on the molecule interact with and/or bind to metal ions when air, water or some other fluid is contacted with, circulated over and/or filtered through the nanocomposite. The metal ions are thereby captured on the surface of the gold nanoparticles.

Raman spectroscopy using SERS enhancement can be used to quantitatively analyze the amount metal present in a sample of the fluid. The Raman spectral features corresponding to the bridging molecule change upon interaction with, capture of or binding to the metal ions, and a comparison of the Raman spectra of a bridging molecule with and without metal present provides a means of indicating the presence of the metal. The amount of metal can be quantified, using appropriate calibration curves. Due to the significant enhancement of the Raman signal from the AuNRs contained on the fibrous mesh, the nanocomposite fiber based sensor is capable of detecting trace amounts of ions in the fluid. This may be useful for determining levels of toxic metals, for example. In some embodiments, the fluid is an environmental fluid sample, such as a water or air sample.

The use of bridging molecules can be extended to analyzing for chemical species in general, including but not limited to soluble or insoluble organic, inorganic, or biological species, including ions, neutral molecules, polymers, proteins, DNA, RNA, viruses, bacteria, and organic or inorganic particulate matter. In each case, the bridging molecule has a moiety capable of binding to the gold nanorods, for example a SH group, and a moiety capable of binding to the target species. In some embodiments, the latter moiety is selected to provide binding via a specific interaction known in the art for the target species. For example, the moiety may be a receptor having binding specificity for a targeted antigen or the like.

Bridging molecules are not needed to detect chemical species in all circumstances, provided that the target species is capable of binding to the gold nanorods. For example, any species comprising SH groups can be bound, including for example biological molecules.

Copper Ion Sensor

A sensor for $Cu^{2+}$ ions was prepared by immersing a AuNR-PCL nanocomposite mesh in a solution of 4-mercaptobenzoic acid (4-MBA) in ethanol, followed by rinsing with ethanol and drying. Varying amounts of $Cu^{2+}$ ions were analyzed by Raman spectroscopy on the sensor, resulting in the spectra shown in FIG. 8 panels a and b.

Figure 8:
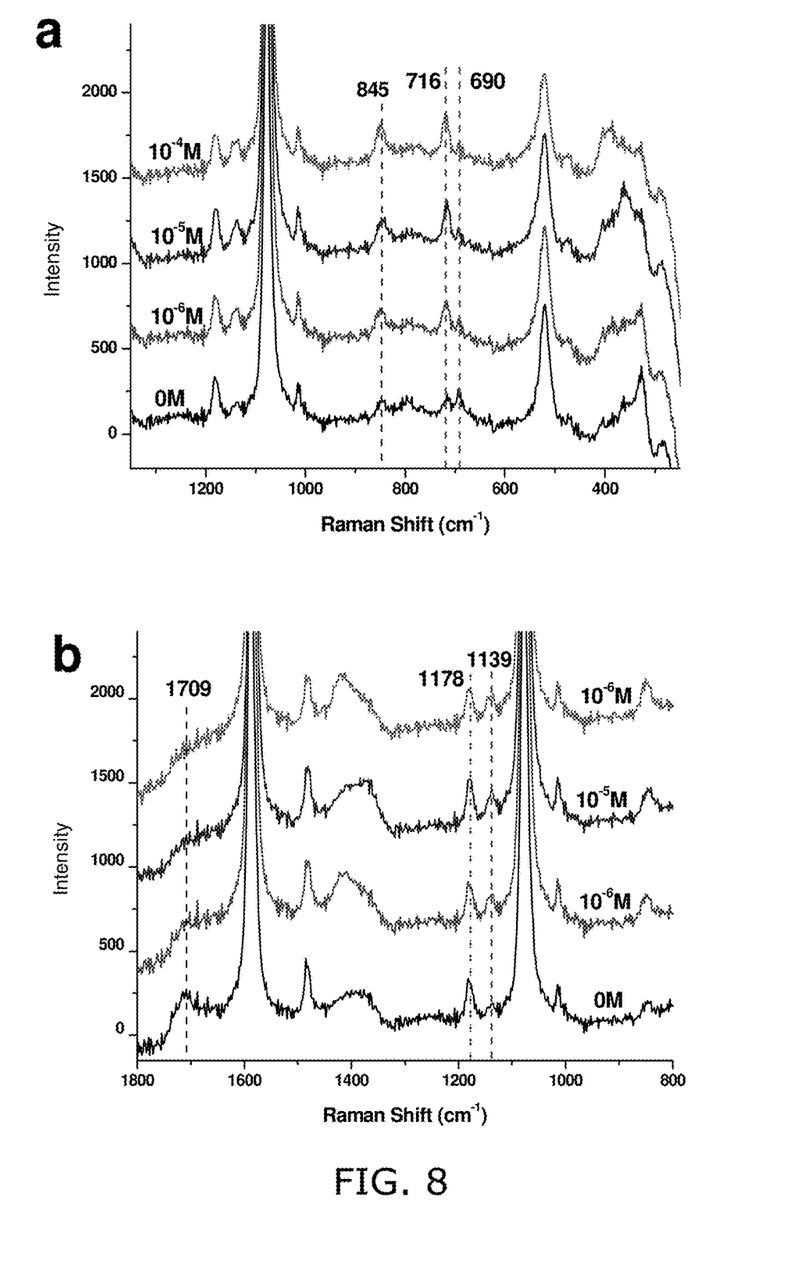
FIG. 8 panels a and b are Raman spectra of a sensor for $Cu^{2+}$ ions according to the invention, taken at various levels of $Cu^{2+}$ ion exposure.

As can be seen, the relative peak intensities of two pairs of peaks (716/690 $cm^{-1}$ and 1178/1139 $cm^{-1}$) change with the change in $Cu^{2+}$ concentration. As the concentration of $Cu^{2+}$ increases, the relative peak intensity of 716/690 $cm^{-1}$ increases while the relative peak intensity of 1178/1139 $cm^{-1}$ decreases.

A calibration curve can be constructed using these data and other spectra obtained at other $Cu^{2+}$ concentrations. A water sample containing $Cu^{2+}$ may be analyzed by contacting the sample with the sensor, rinsing to remove any unbound $Cu^{2+}$, drying, and performing surface enhanced Raman spectroscopy. The $Cu^{2+}$ concentration can then be calculated, using the calibration curve.

Catalyst

In some embodiments, the nanocomposite is a catalyst for a reaction that is catalyzed by gold particles, and the invention therefore provides a method of catalyzing a reaction that includes contacting the nanocomposite with one or more reactants. For example, oxidation of carbon monoxide may be catalyzed by a nanocomposite in which AuNRs are attached to $TiO_2$ fibers by the methods described herein. The $TiO_2$ fibers can be produced by electrospinning and further processing by methods known in the art.

What is claimed is:

1. A nanocomposite structure comprising:
    a) a charged fibrous substrate comprising fibers having disposed on their surfaces a multilayer structure comprising a layer of a first polyelectrolyte and disposed thereon a layer of a second polyelectrolyte of opposite charge from the first, the second polyelectrolyte forming the outermost layer of the charged fibrous substrate; and
    b) charged nanorods having a charge opposite that of the charged fibrous substrate, comprising gold nanorods each having disposed on its surface one or more layers, the outermost of which is a polyelectrolyte layer having a charge opposite that of the layer of second polyelectrolyte on the charged fibrous substrate, wherein the first polyelectrolyte on the charged fibrous substrate and the polyelectrolyte in the outermost layer on the charged nanorods may be the same or different;
    wherein the charged nanorods are disposed unaligned with respect to each other on the charged fibrous substrate.

2. The nanocomposite structure of claim 1, wherein the second polyelectrolyte is cationic.

3. The nanocomposite structure of claim 1, wherein the multilayer structure further comprises one or more additional polyelectrolyte layers, wherein the polyelectrolytes in the additional polyelectrolyte layers may be the same as or different from the first and second polyelectrolyte and wherein the layers of the multilayer structure alternate in charge.

4. The nanocomposite structure of claim 1, further comprising bridging molecules attached to the gold nanorods, wherein each of the bridging molecules comprises a moiety capable of binding to the gold nanorods and a moiety capable of binding to a chemical species.

5. The nanocomposite structure of claim 4, wherein the moiety capable of binding to the gold nanorods is SH.

6. The nanocomposite structure of claim 4, wherein the chemical species is a transition metal ion.

7. The nanocomposite structure of claim 1, wherein the fibers are polycaprolactone fibers.

8. The nanocomposite structure of claim 1, wherein the fibers are electrospun fibers.

9. A method of analyzing for a chemical species, comprising contacting the nanocomposite structure of claim 1 with a fluid comprising the chemical species to bind the chemical species to the nanocomposite structure, and performing surface enhanced Raman spectroscopy on the nanocomposite structure with the bound chemical species.

10. A method of analyzing for metal ions, comprising contacting the nanocomposite structure of claim 4 with a fluid comprising the metal ions to bind metal ions to the nanocomposite structure, and performing surface enhanced Raman spectroscopy on the nanocomposite structure with the bound metal ions.

11. A method of catalyzing a reaction, comprising contacting one or more reactants with the nanocomposite structure of claim 1.

12. A method of making a nanocomposite structure, comprising
    a) providing alternating layers of cationic and anionic polyelectrolytes on the fibers of a fibrous substrate to produce a charged fibrous substrate, the charge of which is defined by the last layer of polyelectrolyte;
    b) applying one or more charged layers to gold nanorods, the outermost layer having a charge opposite that of the charged fibrous substrate; and
    c) contacting the charged fibrous substrate with the nanorods prepared in step b);
    wherein the charged nanorods are disposed unaligned with respect to each other on the charged fibrous substrate.

13. The method of claim 12, further comprising
    d) contacting the nanorods deposited in step c) with a bridging molecule comprising a moiety capable of binding to the gold nanorods and a moiety capable of binding to a chemical species.

14. A method of making a nanocomposite structure, comprising
    a) providing alternating layers of cationic and anionic polyelectrolytes on the fibers of a fibrous substrate to produce a charged fibrous substrate, the charge of which is defined by the last layer of polyelectrolyte;
    b) applying one or more charged layers to gold nanorods, the outermost layer having a charge opposite that of the charged fibrous substrate; and
    c) contacting the charged fibrous substrate with the nanorods prepared in step b);
    wherein the outermost layer on the gold nanorods is a polyelectrolyte layer having a charge opposite that of the layer of second polyelectrolyte on the charged fibrous substrate.

15. The method of claim 14, further comprising
    d) contacting the nanorods deposited in step c) with a bridging molecule comprising a moiety capable of binding to the gold nanorods and a moiety capable of binding to a chemical species.

* * * * *